United States Patent
Tsubota et al.

(10) Patent No.: US 11,369,338 B2
(45) Date of Patent: Jun. 28, 2022

(54) ULTRASONIC CT DEVICE, IMAGE PROCESSING DEVICE, AND IMAGE PROCESSING PROGRAM THAT CORRECTS A SIGNAL OR PIXEL

(71) Applicant: Hitachi, Ltd., Tokyo (JP)

(72) Inventors: Yushi Tsubota, Tokyo (JP); Kenichi Kawabata, Tokyo (JP); Takahide Terada, Tokyo (JP); Atsurou Suzuki, Tokyo (JP); Wenjing Wu, Tokyo (JP); Kazuhiro Yamanaka, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 36 days.

(21) Appl. No.: 16/816,718

(22) Filed: Mar. 12, 2020

(65) Prior Publication Data
US 2021/0030393 A1    Feb. 4, 2021

(30) Foreign Application Priority Data
Jul. 31, 2019   (JP) .............................. JP2019-141628

(51) Int. Cl.
*A61B 8/08*    (2006.01)
*G01S 15/89*   (2006.01)
(Continued)

(52) U.S. Cl.
CPC ............ *A61B 8/0825* (2013.01); *A61B 8/145* (2013.01); *A61B 8/461* (2013.01); *A61B 8/523* (2013.01);
(Continued)

(58) Field of Classification Search
CPC ....... A61B 8/0825; A61B 8/145; A61B 8/461; A61B 8/523; G01S 15/8945; G01S 15/8993
See application file for complete search history.

(56) References Cited

U.S. PATENT DOCUMENTS 6,117,080 A  *  9/2000  Schwartz ............. A61B 8/0825
                                                          600/443
7,218,766 B2 *  5/2007  Eberhard ............... A61B 6/463
                                                          128/922

(Continued)

FOREIGN PATENT DOCUMENTS

JP           3133764 B2    11/2000
JP        2014141398 A  *   8/2014
(Continued)

OTHER PUBLICATIONS

S. Tohnak, et al. "Synthesizing panoramic radiographs by unwrapping dental CT data," Proceedings of the 28th IEEE EMBS Annual International Conference, Aug. 2006 (Year: 2006).*

*Primary Examiner* — Oommen Jacob
*Assistant Examiner* — Nyrobi Celestine
(74) *Attorney, Agent, or Firm* — Mattingly & Malur, PC

(57) ABSTRACT

In an ultrasonic CT device for breast examination, unevenness of an ultrasonic image due to a distribution of inclination angles of a breast is reduced. The distribution of the inclination angles of a surface of a subject in a contour of the subject is obtained from a tomographic image, and a signal level of a reception signal or a pixel value of the tomographic image is corrected using the distribution of the inclination angles.

10 Claims, 11 Drawing Sheets

(51) Int. Cl.
*A61B 8/00* (2006.01)
*A61B 8/14* (2006.01)

(52) U.S. Cl.
CPC ...... *G01S 15/8945* (2013.01); *G01S 15/8993* (2013.01)

(56) References Cited

U.S. PATENT DOCUMENTS

| | | | | |
|---|---|---|---|---|
| 8,600,476 | B2* | 12/2013 | Bi | A61B 5/055 600/415 |
| 9,072,489 | B2* | 7/2015 | Chono | A61B 8/0883 |
| 9,820,710 | B2* | 11/2017 | Ohi | A61B 6/4233 |
| 9,867,595 | B2* | 1/2018 | Sako | A61B 8/4254 |
| 10,520,712 | B2* | 12/2019 | Yuste | G02B 21/002 |
| 10,638,934 | B2* | 5/2020 | Oikawa | A61B 8/4494 |
| 2004/0144176 | A1* | 7/2004 | Yoden | G01S 15/8906 73/628 |
| 2009/0264758 | A1* | 10/2009 | Fujita | A61B 8/406 600/443 |
| 2010/0268088 | A1* | 10/2010 | Prus | A61B 8/14 600/459 |
| 2013/0006114 | A1* | 1/2013 | Pellegretti | A61B 8/0825 600/447 |
| 2014/0058265 | A1* | 2/2014 | Wang | A61B 8/4461 600/447 |
| 2014/0081142 | A1* | 3/2014 | Toma | A61B 8/4245 600/443 |
| 2015/0080726 | A1* | 3/2015 | Yao | A61B 8/5223 600/440 |
| 2015/0104091 | A1* | 4/2015 | Miyasa | G06T 3/0068 382/131 |
| 2015/0221091 | A1* | 8/2015 | Sugiyama | A61B 8/5261 382/131 |
| 2017/0281125 | A1 | 10/2017 | Furukawa et al. | |
| 2018/0310909 | A1* | 11/2018 | Naganawa | A61B 8/4245 |

FOREIGN PATENT DOCUMENTS

| | | |
|---|---|---|
| JP | 2017184972 A | 10/2017 |
| WO | 9528883 A1 | 11/1995 |

* cited by examiner

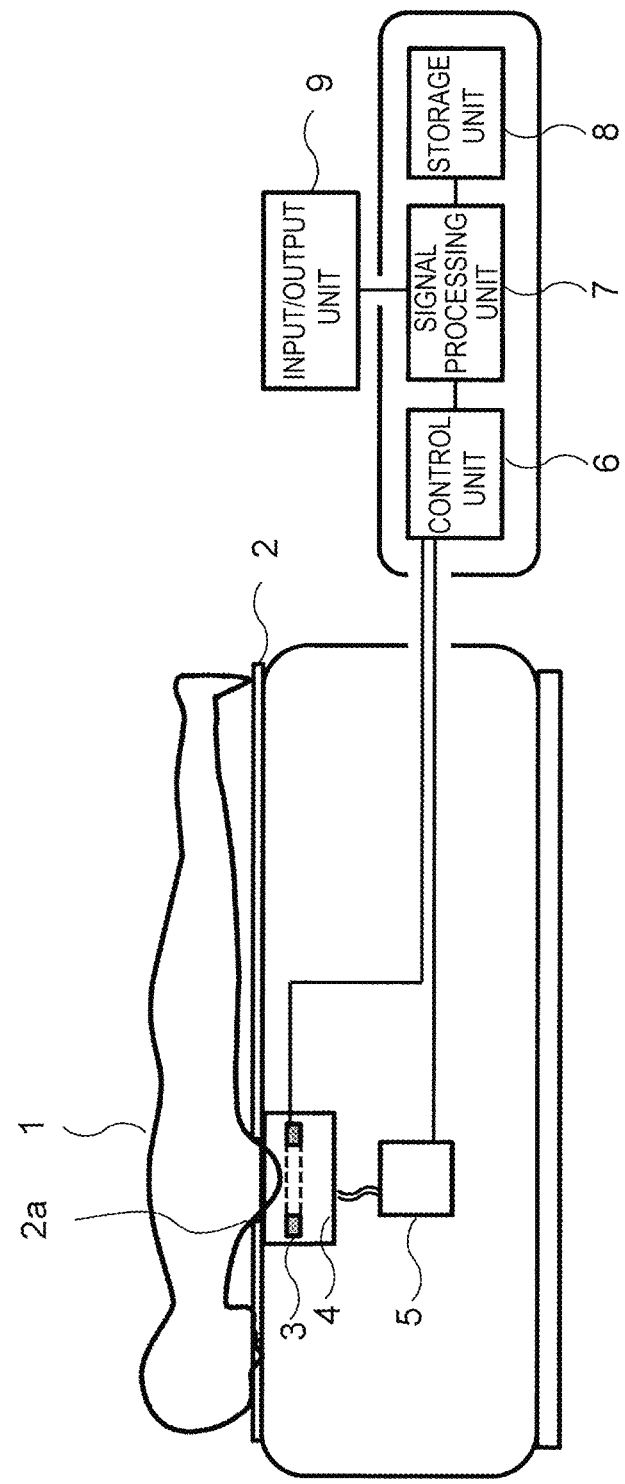
[FIG. 1]

[FIG. 2]
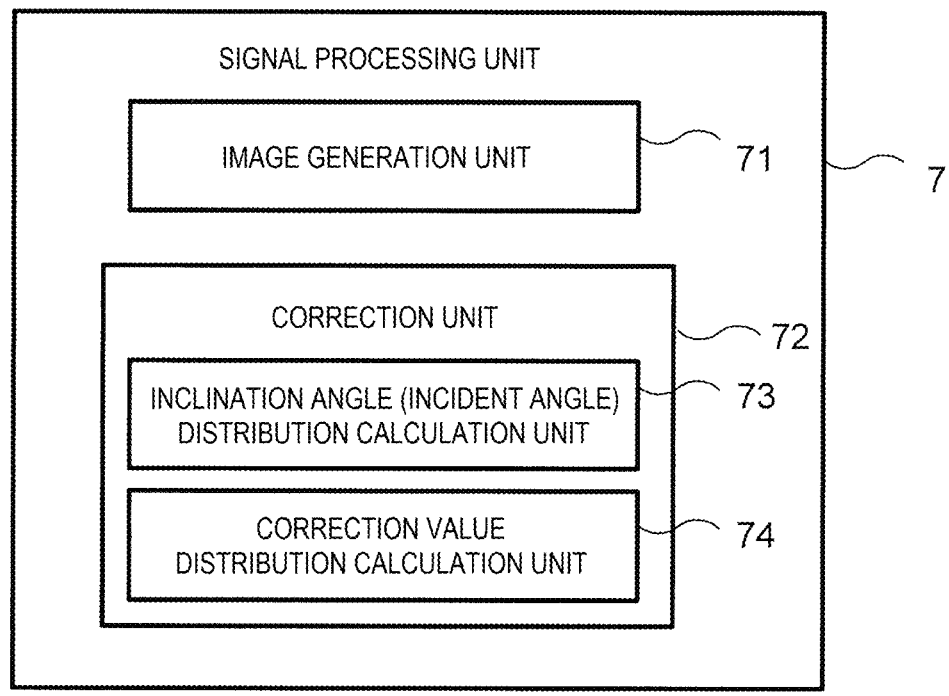

[FIG. 3]
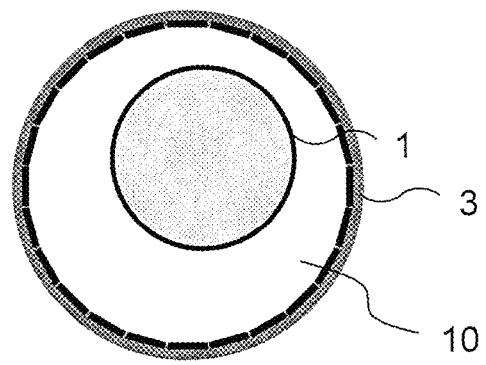

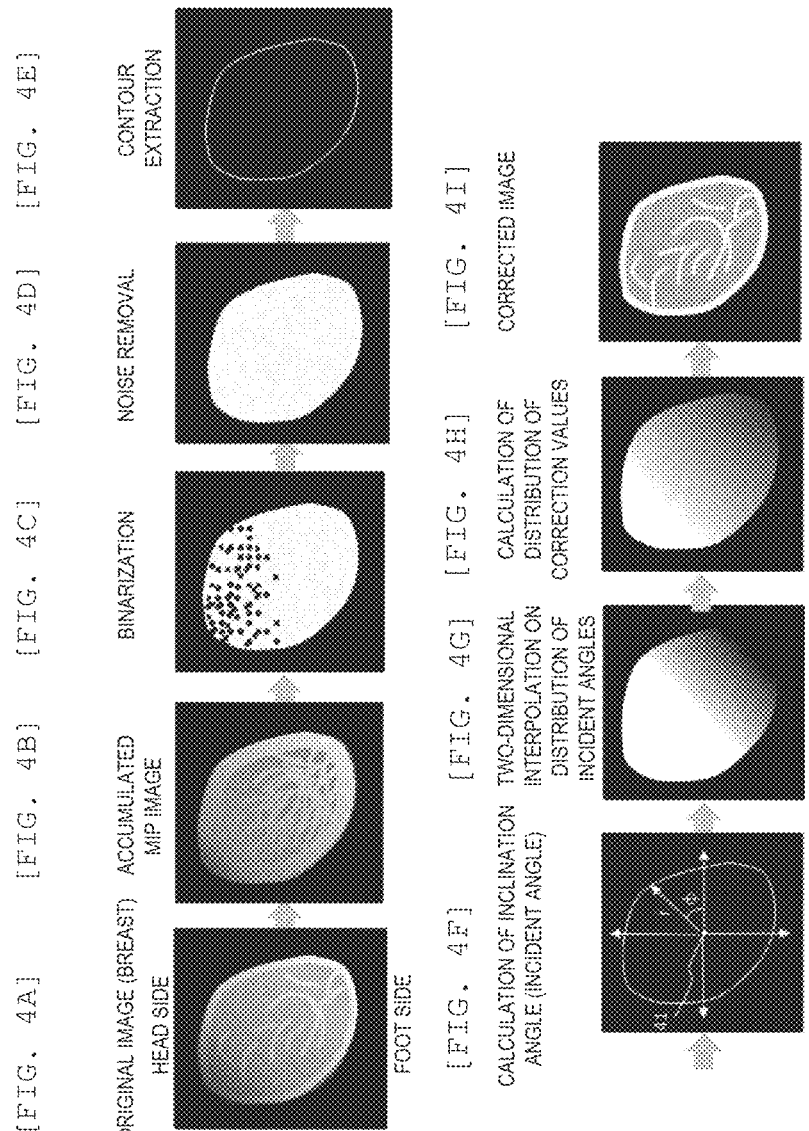

[FIG. 5]
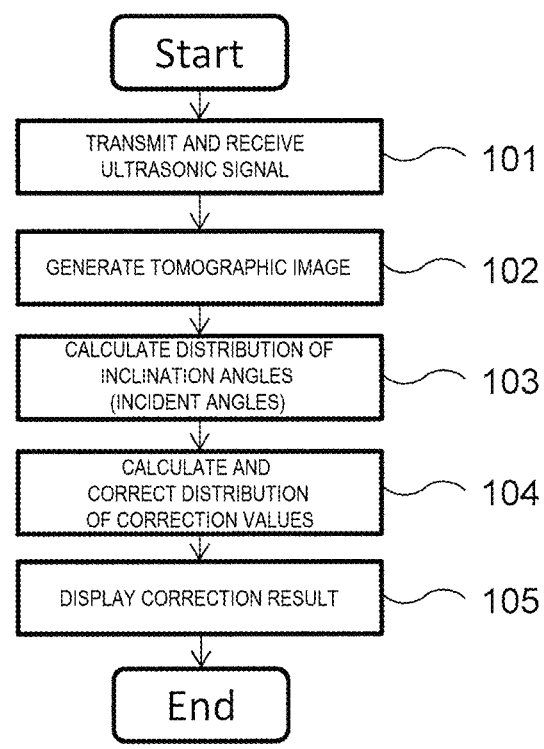

[FIG. 6]
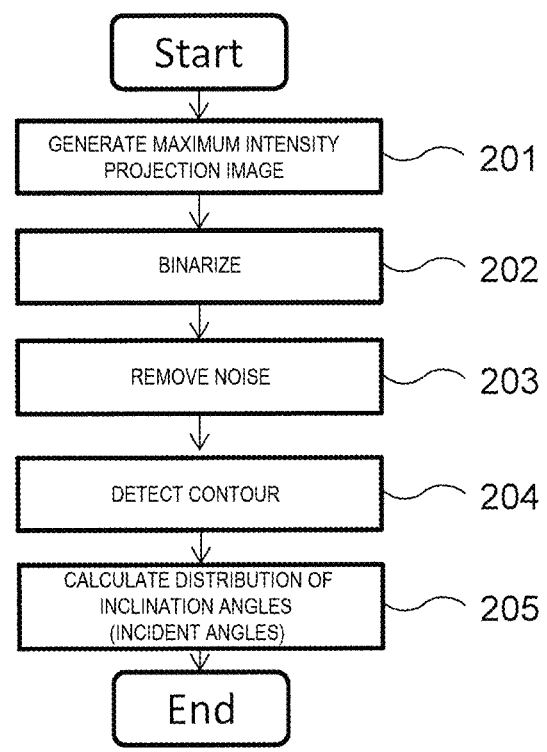

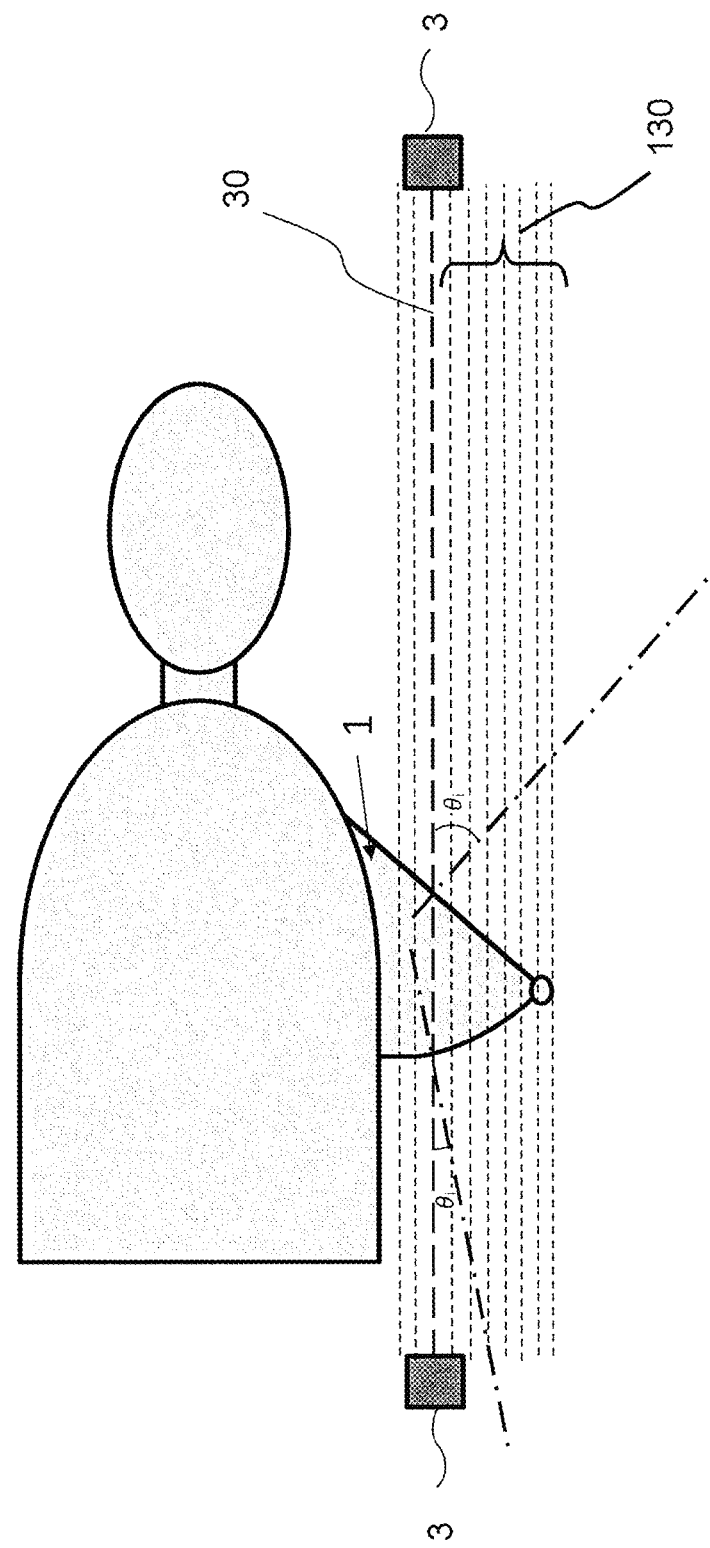
[FIG. 7]

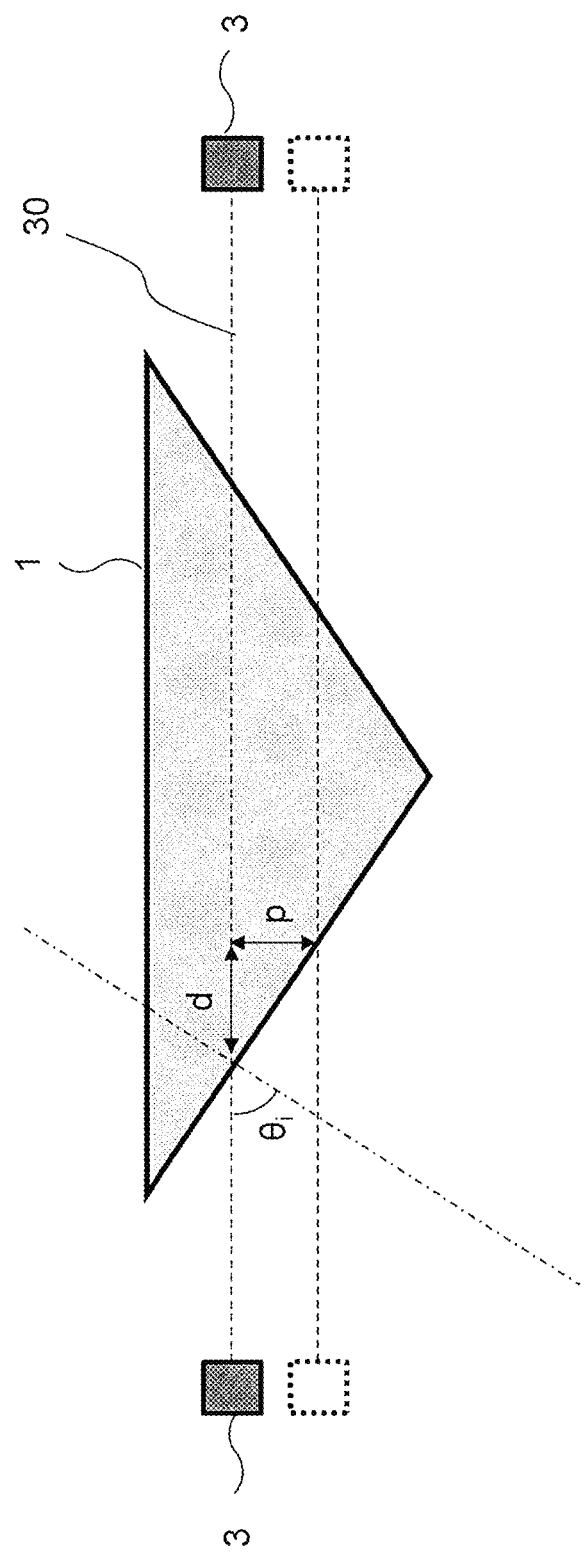

[FIG. 9]
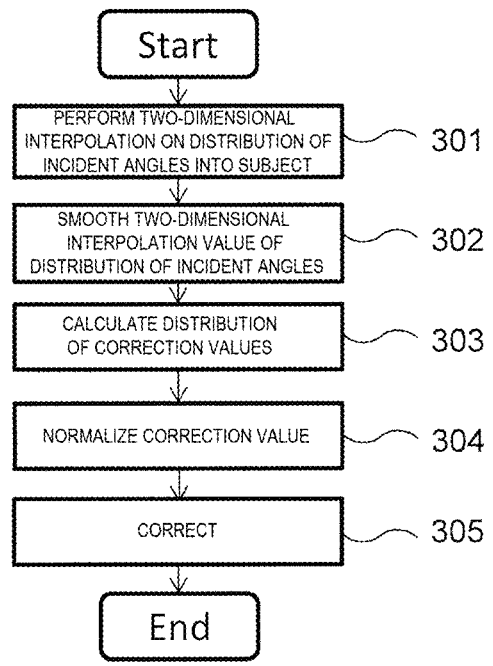

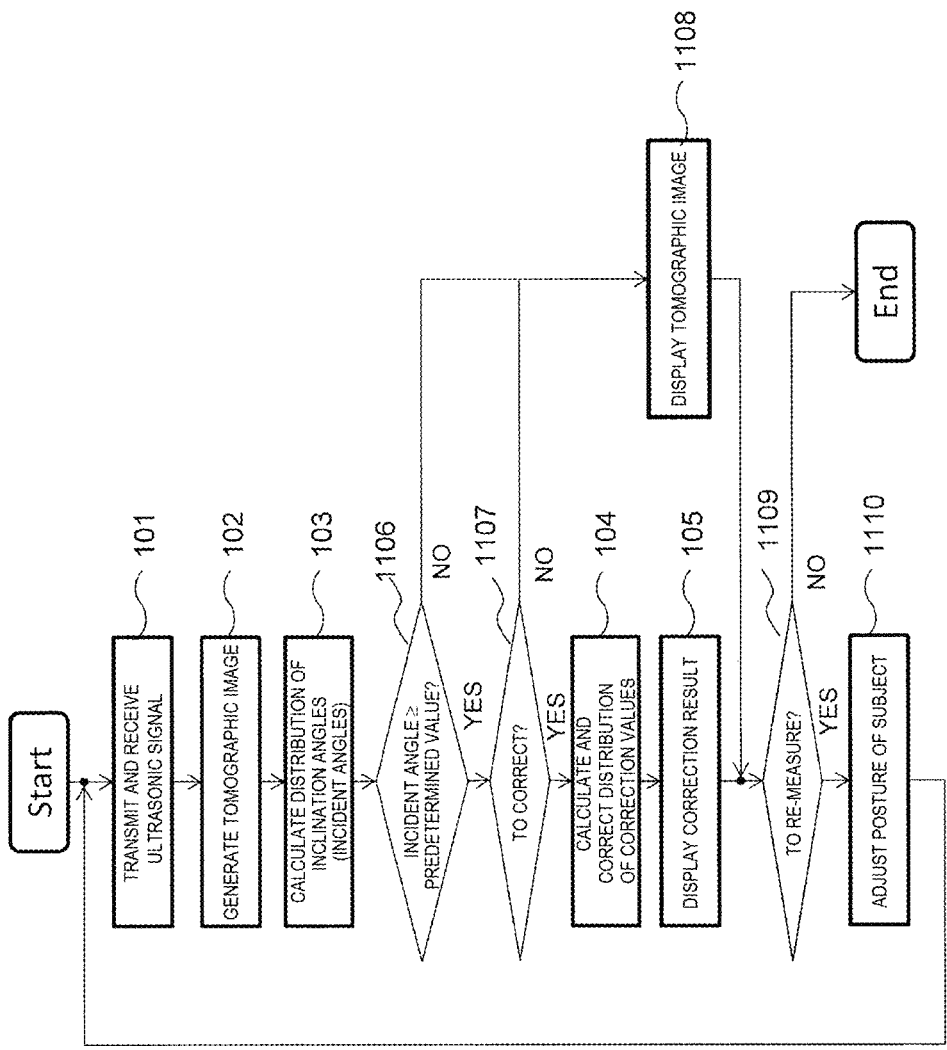
[FIG. 10]

[FIG. 11]
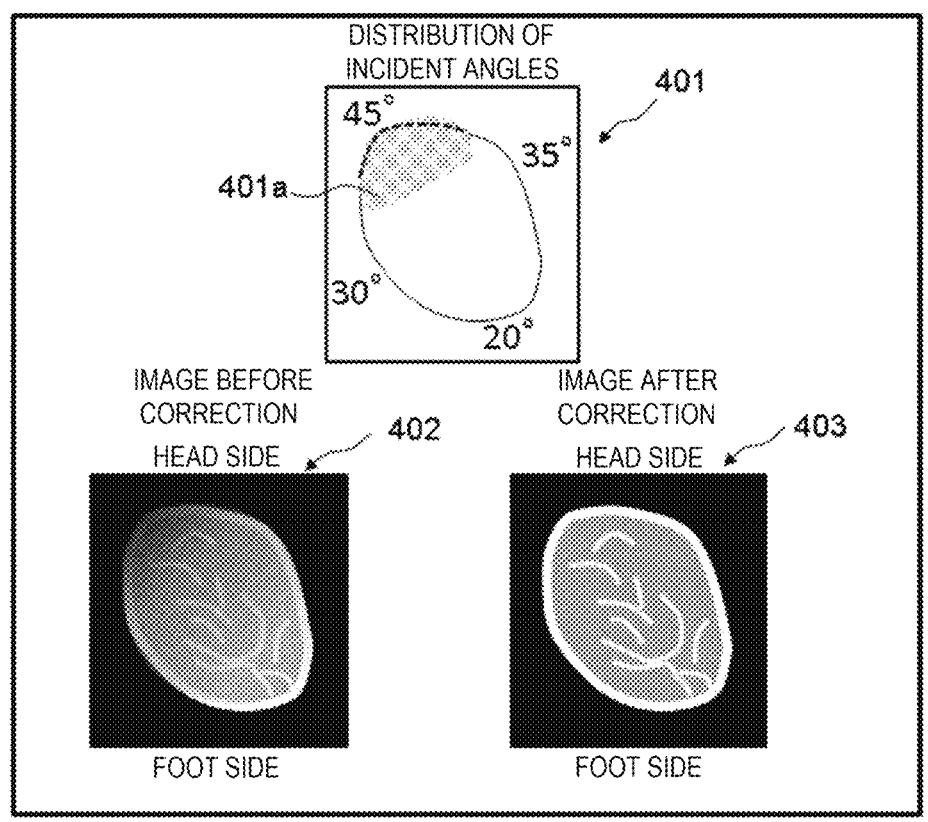

ULTRASONIC CT DEVICE, IMAGE PROCESSING DEVICE, AND IMAGE PROCESSING PROGRAM THAT CORRECTS A SIGNAL OR PIXEL

CROSS-REFERENCE TO RELATED APPLICATION

The present application claims priority from Japanese application JP 2019-141628, filed on Jul. 31, 2019, the contents of which is hereby incorporated by reference into this application.

TECHNICAL FIELD

The present invention relates to an ultrasonic CT device.

BACKGROUND ART

An ultrasonic computed tomography (CT) device is a device that uses a transducer array to irradiate a subject in a medium with an ultrasonic wave from a plurality of directions, receives an ultrasonic wave transmitted through the subject or reflected by the subject with the transducer array, and converts a physical property value (sound speed, attenuation rate, reflectance, or the like) inside the subject from the reception signal into a tomographic image. The transducer array has a structure in which, for example, piezoelectric elements are used as transducers and the transducers are arranged in a ring shape. The subject is inserted into an opening of the ring-shaped transducer array and then photographed. PTL 1 discloses a basic configuration of an ultrasonic CT and an imaging technique.

On the other hand, PTL 2 discloses a device that generates an ultrasonic image by irradiating a subject held by a holding cup with light and receiving an acoustic wave generated in the subject. At this time, in a technique of PTL 2, in order to solve a problem that a waveform is distorted when the acoustic wave passes through a solid in a path where an acoustic wave generated at a position of interest in the subject reaches a receiver, the distorted waveform is corrected by applying a transmission filter to a reception signal.

CITATION LIST

Patent Literature

PTL 1: Japanese Patent No. 3133764
PTL 2: JP-A-2017-184972

SUMMARY OF INVENTION

Technical Problem

In an ultrasonic CT device used for breast examination, a breast is drooped in a prone posture in an opening provided in a bed, and is irradiated with an ultrasonic wave generated from the transducer through a medium such as water. At this time, the ultrasonic wave is emitted in a horizontal direction from the ring-shaped transducer array. However, since a skin surface of the dropped breast is inclined with respect to a vertical direction, the ultrasonic wave is incident obliquely on the skin surface of the breast, and a part of the ultrasonic wave is scattered and deviates from a receiving surface of the transducer array. Thus, an intensity of a reception signal of a reflected wave and a transmitted wave is lowered. In addition, since the dropped breast has a shape that is not centrally symmetric and has different inclination angles depending on the direction, unevenness due to the inclination angle occurs on a reflected wave image and a transmitted wave image.

An object of the invention is to reduce unevenness of an ultrasonic image due to a distribution of inclination angles of a breast.

Solution to Problem

In order to achieve the above object, an ultrasonic CT device of the invention includes: a transducer array configured to irradiate a subject in a medium with an ultrasonic wave from a plurality of directions and receive an ultrasonic wave reflected by the subject and/or an ultrasonic wave transmitted through the subject; an image generation unit configured to generate a tomographic image of the subject using a reception signal of the transducer array; and a correction unit configured to obtain a distribution of inclination angles of a surface of the subject in a contour of the subject from the tomographic image, and correct a signal level of the reception signal or a pixel value of the tomographic image using the distribution of the inclination angles.

Advantageous Effect

According to the invention, by obtaining the distribution of the inclination angles of the surface of the subject in the contour of the subject, unevenness in luminance reduction in the tomographic image due to an oblique incidence of the ultrasonic wave can be corrected with little calculation cost or prevented before an actual measurement, and an image that is easy to interpret for a user can be provided.

BRIEF DESCRIPTION OF DRAWINGS

FIG. 1 is a block diagram showing a schematic structure of a sagittal section of an ultrasonic CT device according to an embodiment of the invention.

FIG. 2 is a functional block diagram showing a configuration of a signal processing unit 7 of the device of FIG. 1.

FIG. 3 is a diagram showing a schematic structure of a coronal section of a transducer array.

FIGS. 4A to 4I are explanatory diagrams showing a processing flow in a correction unit 72 of the device of FIG. 1.

FIG. 5 is a flowchart showing an entire processing flow of the device of FIG. 1.

FIG. 6 is a flowchart showing a processing of an inclination angle (incident angle) calculation unit 73 of FIG. 2.

FIG. 7 is an explanatory diagram showing an incident angle of an ultrasonic wave to a breast and a slice.

FIG. 8 is an explanatory diagram showing a relationship among contour positions of adjacent slices, an inclination of a breast surface, and an incident angle of the ultrasonic wave.

FIG. 9 is a flowchart showing a processing of a correction value distribution calculation unit 74 of FIG. 2.

FIG. 10 is a flowchart showing an entire processing flow of a device according to a modification.

FIG. 11 is an explanatory diagram showing a display screen example according to the modification.

DESCRIPTION OF EMBODIMENTS

Hereinafter, an ultrasonic CT device according to an embodiment of the invention will be described with reference to the drawings.

In the following description, the embodiment in which the ultrasonic CT device is used for breast examination will be described, but an imaging target is not limited to a breast.

<<Main Parts of Ultrasonic CT Device>>

First, main parts of the ultrasonic CT device of the present embodiment will be described.

As shown in FIG. 1, the ultrasonic CT device according to the present embodiment includes a transducer array 3 and a signal processing unit 7. As shown in FIG. 2, the signal processing unit 7 includes an image generation unit 71 and a correction unit 72.

The transducer array 3 is, for example, an array in which transducers are arranged in a ring shape as shown in FIG. 3, and the transducer array 3 irradiates a subject 1 disposed in a medium 10 with an ultrasonic wave from a plurality of directions, and receives an ultrasonic wave reflected by the subject 1 and/or an ultrasonic wave transmitted through the subject 1.

The image generation unit 71 generates a tomographic image of the subject 1 using a reception signal of each transducer of the transducer array 2.

The correction unit 72 obtains a distribution of inclination angles (FIG. 4F) of a surface of the subject 1 in a contour (FIG. 4E) of the subject 1 from the tomographic image (see FIG. 4A), and corrects a signal level of the reception signal or a pixel value of the tomographic image using the distribution of the inclination angles (FIG. 4I).

In this way, in the present embodiment, by obtaining the distribution of the inclination angles of the surface in the contour of the subject 1, unevenness in luminance reduction in the tomographic image due to an oblique incidence of the ultrasonic wave can be corrected with little calculation cost or prevented before an actual measurement, and an image that is easy to interpret for a user can be provided.

Specifically, the correction unit 72 estimates an intensity reduction distribution (FIG. 4G) of the ultrasonic wave in the subject 1 based on the distribution of the inclination angles (FIG. 4F) of the surface of the subject 1, and corrects the signal level of the reception signal or the pixel value of the tomographic image using the estimated intensity reduction distribution of the ultrasonic wave. The correction unit 72 can calculate a distribution of incident angles of the ultrasonic wave to the surface of the subject 1 (FIG. 4F) as the distribution of the inclination angles of the surface of the subject 1.

The correction unit 72 obtains a distribution of values corresponding to the incident angles in the subject 1 by performing two-dimensional interpolation on the calculated distribution of the incident angles of the ultrasonic wave, and estimates the intensity reduction distribution of the ultrasonic wave in the subject 1 based on the distribution of the values corresponding to the incident angles. That is, on the surface of the subject 1, when the incident angle of the ultrasonic wave is large, the intensity reduction of the ultrasonic wave detected by the transducer array 3 is large, and the influence extends even after the ultrasonic wave enters the subject 1, so that the value corresponding to the incident angle inside the subject 1 is calculated by performing two-dimensional interpolation on a value of the incident angle of the ultrasonic wave in the contour of the subject 1. Accordingly, the correction unit 72 estimates the intensity reduction distribution of the ultrasonic wave inside the subject 1.

More specifically, the correction unit 72 calculates a correction value for correcting the intensity reduction distribution of the ultrasonic wave in the subject 1 by using the calculated distribution of the values corresponding to the incident angles, and sound speeds and densities of the medium 10 and the subject 1.

<<Specific Configuration of Ultrasonic CT Device>>

Hereinafter, the ultrasonic CT device of the present embodiment will be specifically described.

FIG. 1 is a schematic structure of a sagittal section of the ultrasonic CT device of the present embodiment. The ultrasonic CT device of the present embodiment includes a bed 2 on which the subject 1 is to be placed, and the bed 2 is provided with an opening 2a into which a breast is inserted. A cylindrical water tank 4 is disposed below the opening 2a. The ring-shaped transducer array 3 as shown in FIG. 3 is provided inside the water tank 4 so as to be movable in parallel in an axial direction of the water tank 4. The transducer array 3 has a configuration in which the transducers such as piezoelectric elements that function as ultrasonic transceivers are arranged in a ring shape. The water tank 4 is filled with warm water. A spare tank 5 is connected to the water tank 4. The spare tank 5 has functions of purifying, overheating and degassing the warm water in the water tank 4.

A control unit 6 and the signal processing unit 7 are connected to the transducer array 3 and the spare tank 5. As shown in a functional block diagram of FIG. 2, the signal processing unit 7 includes the image generation unit 71 and the correction unit 72. The correction unit 72 includes an inclination angle (incident angle) distribution calculation unit 73 and a correction value distribution calculation unit 74. Operations of these units will be described in detail later. An input/output unit 9 and a storage unit 8 are connected to the signal processing unit 7.

The signal processing unit 7 is implemented by a computer and the like including a processor such as a central processing unit (CPU) or a graphics processing unit (GPU) and a memory, and functions of respective units of the signal processing unit 7 are implemented with software by the CPU reading and executing programs stored in the memory. A part of or all the signal processing unit 7 can also be implemented with hardware. A circuit may be designed using a custom IC such as an application specific integrated circuit (ASIC) or a programmable IC such as a field-programmable gate array (FPGA) so as to configure the signal processing unit 7 and implement the functions of respective units of the signal processing unit 7.

Photography conditions of the ultrasonic CT device are set by the user through a touch panel or a keyboard of the input/output unit 9. The set conditions and the like are stored in a memory, a hard disk drive, or the like of the storage unit 8. Based on these conditions, control signals processed by the central processing unit (CPU) or the like of the signal processing unit 7 are sent to various controllers provided in the control unit 6. The controller performs transmission and reception or switching of an ultrasonic signal generated by each transducer of the transducer array 3, control over an up-and-down movement of the transducer array 3, water pressure control and temperature control over the warm water by the spare tank 5, and the like. Reception signals of the reflected wave from the subject 1 and the transmitted wave through the subject 1, which are received by each transducer of the transducer array 3, are recorded in the storage unit 8, and operations such as reconstruction of tomographic images such as reflected wave images and/or transmitted wave images and correction of the tomographic images are performed in the signal processing unit 7. The generated information such as the tomographic image of the subject 1 is displayed on a monitor or the like of the input/output unit 9. The control unit 6, the signal processing unit 7, and the storage unit 8 can be disposed in a space below the bed 2.

<<Operation of Ultrasonic CT Device>>

Operations of the ultrasonic CT device according to the present embodiment will be described. As shown in a flow of FIG. 5, the ultrasonic CT device according to the present embodiment performs the following five processings including: transmitting and receiving the ultrasonic signal from the transducer array 3 to the subject 1 under the control of the control unit 6 (step 101); generating the tomographic image (the reflected wave image and/or the transmitted wave image) (step 102); calculating the distribution of the inclination angles (incident angles) in the contour of the tomographic image (step 103); calculating a distribution of correction values of the tomographic image and correcting the tomographic image using the calculated distribution (step 104); and displaying a correction result (step 105). Hereinafter, the processing will be described in order.

<Step 101: Transmission and Reception of Ultrasonic Signal>

The control unit 6 transmits and receives the ultrasonic signal from the transducer array 3 to the subject 1 (step 101). As a specific example, when a center frequency of the ultrasonic wave emitted from each transducer of the transducer array 3 is 1.5 MHz, a wavelength of the ultrasonic wave in water is about 1 mm. When a pitch of the transducers (piezoelectric elements) is 0.5 mm, the transducer array 3 having a diameter of 326 mm is constituted by 2048 transducer channels. The control unit 6 drives 512 channel transducers of the transducer array 3 to emit an ultrasonic wave of a plane wave having aligned phases, and then a reflected wave is received by the same 512 channel transducers, and a transmitted wave is received by 512 channel transducers that are positioned opposite to the transmission transducers. Therefore, a field of view (FOV) can be secured in a circle having a diameter of 230 mm. The control unit 6 shifts the 512 channel transducers driven on the transducer array 3 by 4 channels to emit a plane wave, and a reflected wave and a transmitted wave are repeatedly received, so that signals of the transmitted wave and the reflected wave from 360 degrees around the subject 1 can be obtained for 512 views whose angles are shifted by 0.7 degrees. When a thickness of the transducer in the axial direction of the water tank 4 is 10 mm, the transducer array 3 is displaced at a pitch of 5 mm in the axial direction of the water tank 4 and the above transmission and reception of the ultrasonic wave is repeated, so that data of 40 slices can be obtained within a displacement of 200 mm. The signal processing unit 7 converts the obtained reception signals (the transmitted wave signal and the reflected wave signal) into digital signals and stores the signals into the storage unit 8.

When generating a transmitted wave image, the above procedure is performed in a state where the subject 1 is inserted and a state where the subject 1 is not inserted, and the signal processing unit 7 stores the transmitted wave signal into the storage unit 8.

<Step 102: Generation of Tomographic Image>

The image generation unit 71 of the signal processing unit 7 generates the tomographic image (step 102).

(Reflected Wave Image)

First, a processing for generating the reflected wave image will be described. The image generation unit 71 of the signal processing unit 7 reads the reception signal of the measured reflected wave from the storage unit 8 and performs Hilbert transform in a time direction. A timing at which the ultrasonic wave returns is obtained by dividing a sum of a distance from the transmission transducer to a target pixel and a distance from the target pixel to a reception transducer by an appropriate sound speed (for example, a sound speed of water). Reception signals obtained at the timing when a signal reflected by the target pixel is estimated to arrive at each of the reception transducers are added. The method is called delay and sum (DAS). By performing the method for all pixels in the field of view, a B-mode image widely used in ultrasonic echo examination can be obtained.

By adding the B-mode images obtained at respective irradiation angles of the same slice, an image (reflected wave image) corresponding to a reflectance distribution of the subject 1 is obtained. The reflected wave image is generated by repeating the above method for each slice.

(Transmitted Wave Image)

Next, a processing for generating the transmitted wave image will be described. The image generation unit 71 of the signal processing unit 7 performs Hilbert transform (envelope detection) in the time direction on the reception signal (reception signal) of the transmitted wave measured for each ultrasonic element, and obtains an arrival time of a peak position of the reception signal to the transducer and a signal intensity at the peak position.

The image generation unit 71 calculates an arrival time difference t before and after an insertion of the subject 1 and a signal intensity ratio (attenuation rate) $\alpha$ by comparing the arrival time and the signal intensity with an arrival time and a signal intensity measured and obtained in advance without inserting the subject 1. The calculation is performed for each view (projection angle) and for each reception transducer (channel). The image generation unit 71 obtains a sinogram of the arrival time difference t by arranging the obtained arrival time difference t in a two-dimensional plane having a view (projection angle) number and a reception transducer (channel) as two axes. Similarly, a sinogram of the signal intensity ratio $\alpha$ is obtained by arranging the obtained signal intensity ratio $\alpha$. The image generation unit 71 obtains these two types of sinograms for each slice.

The image generation unit 71 respectively reconstructs the sinogram of the arrival time difference t and the sinogram of the signal intensity ratio $\alpha$ by a filtered back projection (FBP) or a successive approximation reconstruction method widely used in the field of an X-ray CT device. Accordingly, a sound speed image showing a sound speed distribution in the subject 1 is generated based on the sinogram of the arrival time difference t, and an attenuation rate image showing an attenuation rate distribution is generated based on the sinogram of the signal intensity ratio $\alpha$. Similarly, imaging can be performed with respect to a refractive index or a slowness (an inverse of the sound speed) which is a physical quantity equivalent to the sound speed. The sound speed image, the attenuation rate image, and the like are the transmitted wave images.

<Step 103: Calculation of Distribution of Inclination Angles (Incident Angles)>

An inclination angle (incidence angle) distribution calculation unit (hereinafter referred to as an incident angle distribution calculation unit) 73 of the correction unit 72 calculates the distribution of the inclination angles (the incident angles of the ultrasonic wave) of the surface of the subject 1 in the contour of the tomographic image, which is used for the correction value distribution calculation unit 74 to calculate the correction value. The processing will be described with reference to a flow of FIG. 6. Here, the subject 1 is a dropped breast. Further, an example using a reflected wave image whose contour appears easily and clearly as a tomographic image will be described, but it is of course possible to use a transmitted wave image.

As shown in FIG. 7, for the surface of the breast that is the subject 1, the surface at a head side is generally inclined more than the surface at a foot side with respect to a vertical direction. Therefore, an incident angle $\theta_i$ of the ultrasonic wave emitted from the transducer array 3 in a horizontal direction is larger on a breast surface at the head side than on a breast surface at the foot side, and the intensity of the reflected wave received by the transducer array 3 is reduced. Therefore, as shown in FIG. 4A, in the reflected wave image, a luminance in a region close to the head side (an intensity of the reflected wave signal) is lower than a luminance in a region close to the foot side.

In order to correct such a luminance distribution, in steps 201 to 205, the incident angle distribution calculation unit 73 first extracts the contour of the reflected wave image (FIG. 4A) of a target slice 30 to be corrected. Specifically, the incident angle distribution calculation unit 73 synthesizes the reflected wave image 30 (FIG. 4A) of the target slice 30 and reflected wave images of all slices 130 positioned at a tip (nipple) side. For example, a maximum intensity projection (MIP) image is generated by selecting a maximum value for each corresponding pixel of all reflected wave images to be synthesized (FIG. 4B, step 201). By generating the MIP image in this way, an effect of superimposing the contours of the reflected wave images with a relatively high luminance can be obtained, so that a luminance of a contour region where a luminance of the target slice 30 is low can be increased.

Next, the incident angle distribution calculation unit 73 binarizes the MIP image of FIG. 4B with an appropriate threshold to obtain a binarized image of the subject 1 (FIG. 4C). A processing for removing small structures and noises remaining in the binarized image is performed (step 204). For example, an isolated point is removed by performing well-known hole filling processing or expansion processing from contraction processing.

Next, the incident angle distribution calculation unit 73 can extract the contour of the subject 1 by detecting a boundary of the binarized image using a differential filter or the like (step 204).

The incident angle $\theta_i$ when the ultrasonic wave enters a certain boundary (surface of the breast) can be defined as a three-dimensional angle at which a sound path connecting the transmission transducer, the target pixel, and the reception transducer intersects the boundary, but when the number of the transducers and the pixels increases, it is necessary to calculate the incident angle $\theta_i$ for each combination, and the amount of calculation increases. Further, in order to calculate the incident angle $\theta_i$ more accurately, it is necessary to consider a refraction of the ultrasonic wave at a certain boundary having a sound speed difference, which leads to an increase in calculation cost. Therefore, in the present embodiment, in order to reduce the calculation cost, it is assumed that the intensity reduction of the reflected wave signal received by the transducer array 3 is dominated by a scattering at the boundary (the surface (skin) of the breast), and a representative incident angle of the ultrasonic wave to the boundary (skin surface) is determined.

Specifically, the incident angle distribution calculation unit 73 calculates a center of gravity 41 of a region of the subject 1 surrounded by the contour in FIG. 4E), and obtains polar coordinates $(\varphi, r)$ centered on the center of gravity 41 for pixels on the contour (FIG. 4F). Based on a difference d (that is, a distance between contours of two slices) between a radius r1 of a pixel on a certain contour (polar coordinates $(\varphi1, r1)$) and a radius r2 of a pixel on a contour (coordinates $(\varphi1, r2)$) of adjacent slices having the same deflection angle $\varphi1$ and a slice pitch p, as shown in FIG. 8, an inclination angle of the pixel in a slice direction is given by p/d. Here, since the ultrasonic wave is emitted in a slice plane (horizontal direction), as shown in FIG. 8, the incident angle distribution calculation unit 73 calculates the incident angle $\theta_i$ to a certain pixel on the contour by $\theta_i = |\arctan(d/p)|$.

The incident angle distribution calculation unit 73 calculates a distribution of incident angles by calculating the incident angles $\theta_i$ for all pixels on the contour (step 205).

The distribution of the incident angles may be obtained by changing a plurality of types of thresholds for binarization (step 202), enlargement and reduction ratios for noise removal processing (step 203), and types of filters for contour extraction (step 205), respectively recalculating the incident angles $\theta_i$, and using an average value of the plurality of types of the obtained incident angles $\theta_i$.

In steps 202 to 204, a binarized region is displayed on an output device, the user confirms whether the region is acceptable, and if necessary, the user may manually edit a shape of the binarized region.

<Step 104: Calculation and Correction of Distribution of Correction Values>

The correction value distribution calculation unit 74 calculates the distribution of the correction values of the tomographic image using the distribution of the incident angles in the contour which is calculated by the inclination angle (incident angle) distribution calculation unit 73 (step 104). The processing will be described with reference to a flow of FIG. 9.

As the incident angle $\theta_i$ on the surface of the subject 1 increases, the scattering increases, and the intensity of the reflected wave reflected from the subject 1 and the ultrasonic wave that arrives the transducer array 1 and is detected among the transmitted wave transmitted through the subject 1 is reduced. Therefore, an easy-to-view image in which an influence of a surface shape of the subject 1 is prevented can be obtained by calculating the reduced intensity of the ultrasonic wave based on a value of the incident angle $\theta_i$ and correcting an amplitude of the reception signal or the pixel value of the tomographic image only by the reduced amount.

Here, since what is to be corrected is a tomographic image, it is also necessary to estimate the reduced intensity of the ultrasonic wave inside the subject 1. Therefore, in the present embodiment, since the influence of the intensity reduction of the ultrasonic wave due to the incident angle of the ultrasonic wave on the surface of the subject 1 extends even after the ultrasonic wave enters the subject 1, the value corresponding to the incident angle inside the subject 1 is calculated by performing the two-dimensional interpolation on the value of the incident angle of the ultrasonic wave in the contour of the subject 1. Accordingly, the correction value distribution calculation unit 74 obtains the intensity reduction distribution of the ultrasonic wave inside the subject 1.

Specifically, as shown in FIG. 9, the correction value distribution calculation unit 74 performs the two-dimensional interpolation on the distribution of the incident angles in the contour calculated by the inclination angle (incident angle) distribution calculation unit 73 in step 205 (step 301), and obtains a distribution (estimated distribution of the incident angles) of the values corresponding to the incident angles inside the subject 1 (FIG. 4G). A result of the two-dimensional interpolation of the distribution of the incident angles (FIG. 4G) represents a distribution of the reduction of the ultrasonic signal in the contour and the inside of the subject 1 by the distribution of the incident angles.

Next, the correction value distribution calculation unit 74 performs a smoothing processing on the obtained result of the two-dimensional interpolation of the distribution of the incident angles (step 302).

Further, the correction value distribution calculation unit 74 calculates the distribution of the correction values of the pixel values of the tomographic image using the result of the two-dimensional interpolation of the distribution of the incident angles after smoothing, which represents the distribution of the reduction of the ultrasonic signal. When a sound pressure of an incident wave when a longitudinal wave is incident on a boundary between a medium having an acoustic impedance $z_i$ and a medium having an acoustic impedance $z_t$ is $p_i$, a sound pressure of a transmitted wave is $p_z$, and an amplitude ratio is a sound pressure transmission coefficient T, the sound pressure transmission coefficient T is represented by the following Equation (1) using the incident angle $\theta_i$ and a refraction angle $\theta_t$.

[Equation 1]

$$T = \frac{p_t}{p_i} = \frac{2z_t \cos\theta_i}{z_t \cos\theta_i + z_i \cos\theta_t} \quad (1)$$

The refraction angle $\theta_t$ can be obtained as a function of the incident angle $\theta_i$ by Snell's law (Equation (2) below), where $C_i$ and $C_t$ are sound speeds of the medium having the acoustic impedance $z_i$ and the medium having the acoustic impedance $z_t$, respectively.

[Equation 2]

$$\frac{C_i}{C_t} = \frac{\sin\theta_i}{\sin\theta_t} \quad (2)$$

Therefore, assuming that an ultrasonic wave enters the skin from the warm water as acoustic characteristics of the medium, the sound pressure of the ultrasonic wave is reduced due to incidence on the media having different acoustic characteristics, and luminance reduction occurring in the reflected wave image is $20 \log_{10} T(\theta_i)$ in decibels by using the sound pressure transmission coefficient $T(\theta_i)$ that is a function of the incident angle $\theta_i$.

Therefore, the correction value distribution calculation unit 74 calculates a correction value for correcting the luminance reduction in the reflected wave image by using $-20 \log_{10} T(\theta_i)$ (step 303). However, the incident angle $\theta_i$ is a pixel value of an image (FIG. 4F) which is obtained by performing the smoothing processing on the result of the two-dimensional interpolation of the incident angle $\theta_i$ and obtained in step 302. Accordingly, the correction value distribution calculation unit 74 calculates the distribution of the correction values.

Next, when the ultrasonic wave is perpendicularly incident on the surface of the subject 1 ($\theta_i=0$), the correction value distribution calculation unit 74 normalizes the correction value obtained in step 303 such that the correction value becomes zero (that is, no correction) (step 304). Accordingly, the correction value of each pixel is $-20 \log_{10} T(\theta_i)+20 \log_{10} T(0)$.

Further, since the incident angle is not defined for a region outside the binarized subject 1, the correction value distribution calculation unit 74 extrapolates the correction value to the region outside the binarized subject 1 or sets the correction value to 0 or NaN value.

The correction value distribution calculation unit 74 adds the correction value to the reflected wave image (step 305). Accordingly, the intensity of the ultrasonic wave that has been reduced depending on the incident angle $\theta_i$ can be corrected, and a reflected wave image without luminance unevenness can be obtained as shown in FIG. 4I.

In a case where a cross-sectional area of the subject is small, such as near the nipple, even if the reflected signal is near the skin surface, the luminance reduction is relatively small due to an influence of synthesizing the reflected signals from a plurality of different angles. In this case, normalization depending on a cross-sectional area A of the subject may be performed. That is, f(A) may be added to the correction value in the normalization (step 304). As the function f, a polynomial such as a quadratic function may be used.

In step 305, a physical property value indicated by the transmitted wave image may be corrected by adding the correction value to the transmitted wave image. However, when correcting the transmitted wave image, in steps 303 and 304, a correction value for correcting the physical property value is calculated based on the result of the two-dimensional interpolation of the distribution of the incident angles.

<Step 105: Display of Correction Result>

Finally, the correction value distribution calculation unit 74 displays a corrected image on a display unit of the input/output unit 9 (step 105 in FIG. 5).

As described above, in the ultrasonic CT device of the present embodiment, luminance reduction in the reflected wave image due to the oblique incidence of the ultrasonic wave can be corrected with little calculation cost or prevented before the actual measurement, and an image that is easy to interpret for the user can be provided.

In step 103, the inclination angle (incident angle) distribution calculation unit 73 obtains the incident angle based on the inclination angle, and in step 104, the correction value distribution calculation unit 74 calculates the distribution of the correction values based on the distribution of the incident angles. Alternatively, in step 103, the inclination angle (incident angle) distribution calculation unit 73 may calculate the inclination angle, and in step 104, the correction value distribution calculation unit 74 may directly calculate the distribution of the correction values based on the inclination angle.

<<Modification>>

In the above-described embodiment, the corrected image is generated every time a tomographic image is generated. However, it is also possible to adopt a configuration in which the user can switch whether to apply the correction.

For example, as shown in a flow of FIG. 10, the inclination angle (incident angle) distribution calculation unit 73 calculates the distribution of the inclination angles (incident angles) in the contour of the subject 1 by performing steps 101 to 103 of FIG. 5, and then the correction unit 72 determines whether the calculated incident angle has a value equal to or larger than a predetermined value (for example, 40°) (step 1106). If the incident angle is equal to or larger than the predetermined position, the correction unit 72 displays a display asking the user whether to make a correction (step 1107).

If the user inputs an intention to perform the correction via the input/output unit 9, the processing proceeds to step 104, and the correction value distribution calculation unit 74 calculates the distribution of the correction values, corrects the tomographic image, and displays the corrected image on the display unit (steps 104 and 105).

FIG. 11 shows an example of a display screen displaying the corrected image. On the display screen of FIG. 11, a tomographic image after the correction (reflected wave image) 403 and a tomographic image before the correction (reflected wave image) 402 are displayed side by side, and the user can compare the images before and after the correction.

Further, an image 401 of the distribution of the incident angles in the contour calculated in step 103 is also displayed on the display screen of FIG. 11, and the user can confirm the distribution of the incident angles. In the image 401 of the distribution of the incident angles, a region 401a where the incident angle is equal to or larger than the threshold is highlighted by coloring or the like. The image 401 of the distribution of the incident angles may be displayed to be superimposed on the tomographic image 402, 403 before or after the correction.

Further, after step 105, the correction unit 72 displays a display asking the user whether to perform re-measurement (step 1109). At this time, in step 1106, if a value of the incident angle in the distribution of the incident angles is equal to or larger than the predetermined value (for example, 40°), in step 1109, the correction unit 72 may display a message prompting the re-measurement to be performed, or may reproduce a sound.

If the user selects to perform the re-measurement via the input/output unit 9, the correction unit 72 adjusts a posture of the subject 1 so as to reduce a portion where the incident angle of the subject 1 is large, and then prompts the user to perform the re-measurement (step 1110). Then, the processing returns to step 101 to perform the re-measurement.

In step 1106, if all the incident angles in the distribution of the incident angles are smaller than the predetermined value, and in step 1107, if the user selects not to perform the correction, the correction unit 72 proceeds to step 1108, and displays the tomographic image generated in step 102 on the display unit.

Further, in step 1107, if the user selects to perform the correction, the user may be configured to be able to input (set) an applied strength β of the correction via the input/output unit 9. If the user inputs the applied strength β of the correction, in step 104, the correction value distribution calculation unit 74 adjusts the strength of the correction value by, for example, multiplying the correction value by the applied strength β of the correction.

In the above-described embodiment, the correction unit 72 is provided in the signal processing unit 7 of the ultrasonic CT device, and is configured to correct the tomographic image, but the ultrasonic CT device that obtains data and a device that performs the processing of the correction unit 72 may be different devices.

In this case, it is also possible to adopt a configuration in which only the correction is performed by another correction device. Further, ultrasonic reception data obtained by the ultrasonic CT device is received, and is transferred to an image processing device including the signal processing unit 7, the storage unit 8, and the input/output unit 9, and the image processing device may be configured to perform the generation and the correction of the tomographic image in steps 102 to 105 in FIG. 5.

REFERENCE SIGN LIST

1: subject
2: bed
3: transducer array
4: water tank
5: spare tank
6: control unit
7: signal processing unit
8: storage unit
9: input/output unit

The invention claimed is:

1. An ultrasonic CT device, comprising:
a transducer array, which includes a transmission transducer and a reception transducer, configured to irradiate a subject in a medium with an ultrasonic wave from a plurality of directions and receive an ultrasonic wave reflected by the subject and/or an ultrasonic wave transmitted through the subject;
an image generation unit configured to generate a tomographic image of the subject using a reception signal of the transducer array; and
a correction unit configured to generate a maximum intensity projection (MIP) image by selecting a maximum value for each corresponding pixel of all reflected wave images to be synthesized and binarize the MIP image based on a threshold to obtain a binarized image of the subject and extract a contour of the subject by detecting a boundary of the binarized image using a differential filter and obtain a distribution of incident angles of the ultrasonic wave to a surface of the subject in the contour of the subject from the tomographic image by calculating the incident angles for all pixels on the contour, and correct a pixel value of the tomographic image based on the distribution of the incident angles, wherein the correction unit is configured to estimate an intensity reduction distribution of the ultrasonic wave in the subject based on the distribution of the incident angles of the surface of the subject, and correct the pixel value of the tomographic image based on the estimated intensity reduction distribution of the ultrasonic wave,
wherein the incident angles are defined as three-dimensional angles at which a sound path connecting the transmission transducer, a target pixel, and the reception transducer intersects the boundary,
wherein the correction unit is configured to obtain a distribution of values corresponding to the incident angles in the subject by performing two-dimensional interpolation on the distribution of the incident angles of the ultrasonic wave in the contour of the subject, and estimate the intensity reduction distribution of the ultrasonic wave in the subject based on the distribution of the values corresponding to the incident angles,
wherein the correction unit is configured to obtain, for each position in the subject, a correction value for correcting the intensity reduction distribution of the ultrasonic wave in the subject based on sound speeds and densities of the medium and the subject and the distribution of the values corresponding to the incident angles, and
wherein the correction unit is configured to calculate the incidence angle of the surface of the subject based on a distance between contours of two or more tomographic images having different slice positions.

2. The ultrasonic CT device according to claim 1,
wherein the correction unit is configured to calculate the contour of the subject from the tomographic image.

3. The ultrasonic CT device according to claim 2,
wherein when the subject is a breast, the correction unit is configured to synthesize the tomographic image whose contour is to be calculated with tomographic images of one or more slices whose slice positions are closer to a nipple than that of the tomographic image, and extract the contour from the synthesized tomographic image.

4. The ultrasonic CT device according to claim 1,
wherein the correction unit is configured to calculate the correction value as a function having a correction term that is based on a cross-sectional area of the subject.

5. The ultrasonic CT device according to claim 1,
wherein the correction unit is configured to display the tomographic image before correction and a tomographic image after the correction on a display unit connected thereto.

6. The ultrasonic CT device according to claim 1, further comprising:
a receiving unit configured to receive, from a user, a setting of an applied strength of correction of the correction unit,
wherein the correction unit is configured to adjust the correction value according to the applied strength received by the receiving unit.

7. The ultrasonic CT device according to claim 1,
wherein the correction unit is configured to display the calculated distribution of the incident angles on a display unit connected thereto.

8. The ultrasonic CT device according to claim 1,
wherein when the calculated incident angle exceeds a predetermined threshold, the correction unit notifies the user of the above.

9. An image processing device, comprising:
an image generation unit configured to receive a reception signal that receives an ultrasonic wave reflected by a subject irradiated with an ultrasonic wave from a plurality of directions and/or an ultrasonic wave transmitted through the subject, and generate a tomographic image of the subject, the subject irradiated with the ultrasonic wave from a transmission transducer and the reception signal received by a reception transducer; and
a correction unit configured to generate a maximum intensity projection (MIP) image by selecting a maximum value for each corresponding pixel of all reflected wave images to be synthesized and binarize the MIP image based on a threshold to obtain a binarized image of the subject and extract a contour of the subject by detecting a boundary of the binarized image using a differential filter and obtain a distribution of incident angles of the ultrasonic wave to a surface of the subject in the contour of the subject from the tomographic image by calculating the incident angles for all pixels on the contour, and correct a pixel value of the tomographic image based on the distribution of the incident angles,
wherein the incident angles are defined as three-dimensional angles at which a sound path connecting the transmission transducer, a target pixel, and the reception transducer intersects the boundary,
wherein the correction unit is configured to estimate an intensity reduction distribution of the ultrasonic wave in the subject based on the distribution of the incident angles of the surface of the subject, and correct the pixel value of the tomographic image based on the estimated intensity reduction distribution of the ultrasonic wave,
wherein the correction unit is configured to obtain a distribution of values corresponding to the incident angles in the subject by performing two-dimensional interpolation on the distribution of the incident angles of the ultrasonic wave in the contour of the subject, and estimate the intensity reduction distribution of the ultrasonic wave in the subject based on the distribution of the values corresponding to the incident angles,
wherein the correction unit is configured to obtain, for each position in the subject, a correction value for correcting the intensity reduction distribution of the ultrasonic wave in the subject based on sound speeds and densities of the medium and the subject and the distribution of the values corresponding to the incident angles, and
wherein the correction unit is configured to calculate the incidence angle of the surface of the subject based on a distance between contours of two or more tomographic images having different slice positions.

10. A non-transitory computer readable medium storing an image processing program that causes a computer to execute steps comprising:
generating, by an image generator, a tomographic image of a subject from a reception signal that receives an ultrasonic wave reflected by the subject irradiated with an ultrasonic wave from a plurality of directions and/or an ultrasonic wave transmitted through the subject, and generating a tomographic image of the subject, the subject irradiated with the ultrasonic wave from a transmission transducer and the reception signal received by a reception transducer; and
generating a maximum intensity projection (MIP) image by selecting a maximum value for each corresponding pixel of all reflected wave images to be synthesized and binarize the MIP image based on a threshold to obtain a binarized image of the subject and extract a contour of the subject by detecting a boundary of the binarized image using a differential filter;
obtaining, by a correction unit, a distribution of incident angles of the ultrasonic wave to a surface of the subject in the contour of the subject from the tomographic image by calculating the incident angles for all pixels on the contour, and correcting a pixel value of the tomographic image using the distribution of the inclination angles,
wherein the incident angles are defined as three-dimensional angles at which a sound path connecting the transmission transducer, a target pixel, and the reception transducer intersects the boundary,
wherein the correction unit is configured to estimate an intensity reduction distribution of the ultrasonic wave in the subject based on the distribution of the incident angles of the surface of the subject, and correct the pixel value of the tomographic image based on the estimated intensity reduction distribution of the ultrasonic wave,
wherein the correction unit is configured to obtain a distribution of values corresponding to the incident angles in the subject by performing two-dimensional interpolation on the distribution of the incident angles of the ultrasonic wave in the contour of the subject, and estimate the intensity reduction distribution of the ultrasonic wave in the subject based on the distribution of the values corresponding to the incident angles, wherein the correction unit is configured to obtain, for each position in the subject, a correction value for correcting the intensity reduction distribution of the ultrasonic wave in the subject based on sound speeds and densities of the medium and the subject and the distribution of the values corresponding to the incident angles, and wherein the correction unit is configured to calculate the incidence angle of the surface of the subject based on a distance between contours of two or more tomographic images having different slice positions.

\* \* \* \* \*